(12) United States Patent
Hörnig

(10) Patent No.: US 8,498,868 B2
(45) Date of Patent: Jul. 30, 2013

(54) TECHNICAL MEDICAL SYSTEM AND METHOD FOR OPERATING IT

(75) Inventor: Mathias Hörnig, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1131 days.

(21) Appl. No.: 11/890,401

(22) Filed: Aug. 6, 2007

(65) Prior Publication Data

US 2008/0039818 A1 Feb. 14, 2008

(30) Foreign Application Priority Data

Aug. 11, 2006 (DE) .......................... 10 2006 037 775

(51) Int. Cl.
*G10L 21/00* (2006.01)
*A61B 5/00* (2006.01)
*A61B 8/14* (2006.01)

(52) U.S. Cl.
USPC ........ 704/270; 704/270.1; 704/275; 600/300; 600/301; 600/463

(58) Field of Classification Search
USPC ............... 704/270, 270.1, 275; 600/300, 301, 600/601, 463
See application file for complete search history.

(56) References Cited

U.S. PATENT DOCUMENTS

| | | | | |
|---|---|---|---|---|
| 5,876,325 A | * | 3/1999 | Mizuno et al. | 600/102 |
| 7,257,531 B2 | * | 8/2007 | Holub | 704/235 |
| 7,997,903 B2 | * | 8/2011 | Hasson et al. | 434/262 |
| 8,002,767 B2 | * | 8/2011 | Sanchez et al. | 606/1 |
| 2003/0060808 A1 | * | 3/2003 | Wilk | 606/1 |
| 2004/0034302 A1 | * | 2/2004 | Abovitz et al. | 600/428 |
| 2004/0106916 A1 | * | 6/2004 | Quaid et al. | 606/1 |
| 2004/0116908 A1 | * | 6/2004 | Birkenbach et al. | 606/1 |
| 2005/0084833 A1 | * | 4/2005 | Lacey et al. | 434/262 |
| 2005/0206583 A1 | * | 9/2005 | Lemelson et al. | 345/7 |
| 2006/0100497 A1 | * | 5/2006 | Sawazaki et al. | 600/407 |
| 2006/0142739 A1 | * | 6/2006 | DiSilestro et al. | 606/1 |
| 2006/0142740 A1 | * | 6/2006 | Sherman et al. | 606/1 |
| 2006/0190263 A1 | * | 8/2006 | Finke et al. | 704/270 |
| 2008/0033410 A1 | * | 2/2008 | Rastegar et al. | 606/9 |

FOREIGN PATENT DOCUMENTS

DE 196 31 589 A1 2/1998
DE 198 14 095 A1 10/1999

OTHER PUBLICATIONS

S. Grange, T.W. Fong, and C. Baur, "MORIS: Medical/Operating Room Interaction System", International Conference on Multimodal Interfaces (ICMI), ACM, 2004.*
Leventon, M. E. (1997). A Registration, Tracking, and Visualization System for Image-Guided Surgery (Doctoral dissertation, Massachusetts Institute of Technology).*

* cited by examiner

*Primary Examiner* — Edgar Guerra-Erazo

(57) ABSTRACT

The invention relates to a method for operating a technical medical system during a medical procedure, wherein a parameter correlated with the quality of the performance of the procedure is continuously registered while the procedure is being performed, the parameter is evaluated based on a quality criterion correlated with the procedure's fault-free performance, and an auxiliary procedure for the medical procedure is initiated as soon as the parameter has violated the quality criterion. The invention also relates to a technical medical system for performing a medical procedure according to the inventive method.

20 Claims, 2 Drawing Sheets

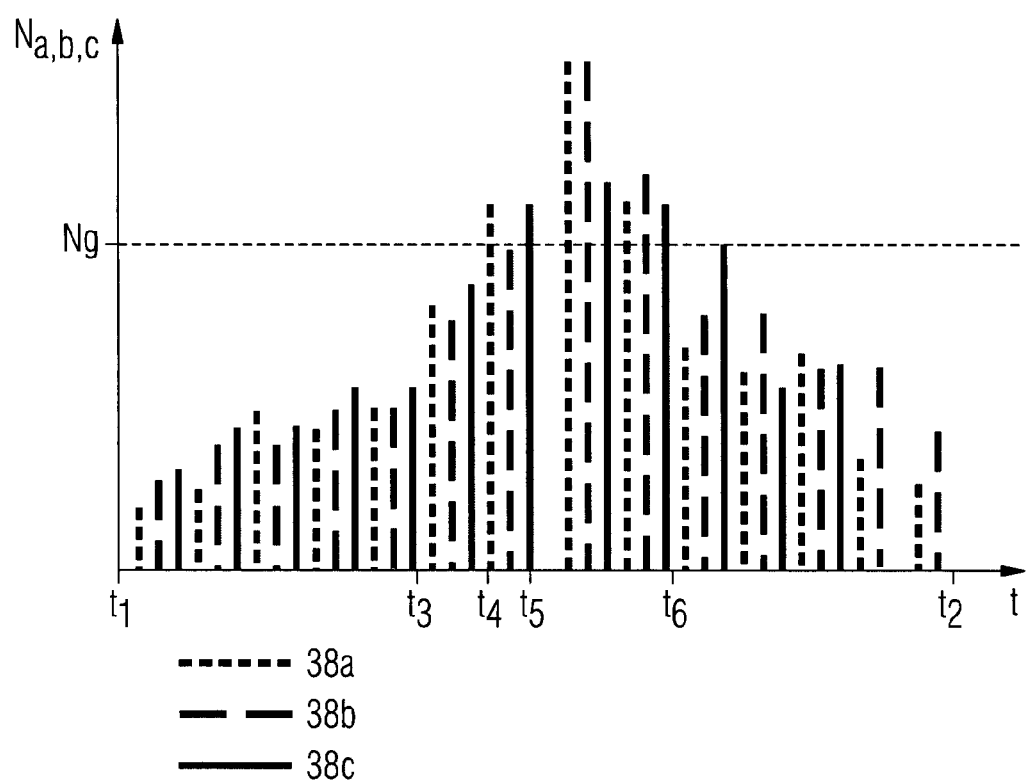

TECHNICAL MEDICAL SYSTEM AND METHOD FOR OPERATING IT

CROSS REFERENCE TO RELATED APPLICATIONS

This application claims priority of German application No. 10 2006 037 775.3 filed Aug. 11, 2006, which is incorporated by reference herein in its entirety.

FIELD OF THE INVENTION

The invention relates to a method for operating a technical medical system during a medical procedure being performed therewith by an operator and to a corresponding technical medical system.

BACKGROUND OF THE INVENTION

Highly complex devices such as, for example, technical systems for medical interventions are now available for numerous applications in medicine. An exemplary instance thereof is PTCA (Percutaneous Transluminal Coronary Angiography). Owing to the high complexity of such systems, incorrect system operation by the operator while the medical procedures are being performed cannot be precluded. That will in the worst case result in the patient's being treated incorrectly. Incorrect operation can be due to, for example, complications arising during the medical procedure such as, for instance, bleeding from the patient, depending on how far the individual steps in the medical procedure have progressed. Other, for example external factors such as, for instance, the operator's emotional state (stress, nervousness, strain) are also possible causes of incorrect operation.

It would be desirable for signs of behavioral or operational actions due to, for example, stress or complications to be identified, particularly by the technical medical system itself, and for steps consequently to be optionally initiated in order to reduce said actions that are due to stress or complications and to provide assistance for the operator, for example. That, too, can be provided by the technical medical system.

SUMMARY OF THE INVENTION

The object of the present invention is hence to disclose both an improved method for operating a technical medical system and a correspondingly improved technical medical system.

Said object is achieved in terms of the method by means of a method according to the claims.

A parameter is accordingly continuously registered during the medical procedure being performed by an operator with the technical medical system; in other words: The parameter is tracked or observed uninterruptedly throughout the entire medical procedure. In terms of the parameter's being registered digitally, that can of course take place at discrete instants following temporally adequately in close succession. The nature of the parameter is therein such that it will provide information about the quality of the performance of the medical procedure; in other words, the parameter will thus reveal whether the medical procedure is proceeding or being performed in any way exceptionally or unusually, or as expected. The parameter can therein also reveal whether the operator is behaving as expected or in an unusual or conspicuous manner, or is operating the medical system accordingly.

Because the parameter will hence provide information about the quality of the procedure, relevant quality criteria reflecting conditions for the parameter can also be found for assessing, on the basis of the parameter, whether the procedure is proceeding smoothly, namely through its evaluation based on the quality criterion.

If the parameter then violates the quality criterion, it can be assumed that the procedure's performance quality is inadequate or that the medical procedure is not being performed according to normal practice. Auxiliary procedures for the medical procedure will hence be inventively initiated. The purpose of said auxiliary procedures is to help the operator to return to performing the medical procedure in accordance with normal practice or to protect the patient on whom the procedure is being performed. Continuous registering of the parameter will thus result in the automatic detection of behavior due to stress or complications at what are as a rule complex medical devices. What is provided by the auxiliary procedure is assistance that will reduce stress or is workflow-oriented in terms of the specific medical procedure, thereby establishing a favorable system environment for the operator. It will therefore be detected on the system automatically whether a stress-related or problematic situation has arisen which, through the system's then reacting appropriately, will be mollified in order to safeguard the patient.

That will finally foster patient confidence since patients will be better safeguarded against operator errors and hence injury. Thus the operator will in the case of, for instance, highly irradiative interventions or operations be prevented from applying a dose that is unusually high for a specific treatment or from repeatedly X-raying the same region of a patient's body unusually frequently or for an unwanted length of time.

The inventive method will thus enable an in some way "peculiar" system operation to be detected. Thanks to the auxiliary procedure it will moreover be possible to restore the procedure to being performed "according to normal practice".

Not just one but, as a rule, a plurality of parameters are in most cases registered. The auxiliary procedure will start being initiated whenever, for example, at least two of the parameters violate the quality criterion.

In keeping with what has been stated above, there are various possibilities for the parameter.

For example the number of operator interactions with the system can be registered as a parameter. Interactions are, for instance, key actuations, movements of a joystick, the number of angulations in the case of a C-arm X-ray system, the dwell time at one angulation, the number of images of the patient obtained during each unit of time, the number of eyelid movements performed by the operator, determined through, for example, camera monitoring, or how often the patient is repositioned during a specific time interval. Continuous registering of the parameter will thus enable the number of interactions during each unit of time to be tracked.

A maximum number of interactions during each time interval can thus be evaluated as the quality criterion. Thus, for example, a significant increase in the number of said interactions during a specific therapeutic step will be detected. The mean number of actions per minute, for example, can be stored user-specifically as the basis for a quality criterion of said type. Experimental values obtained from earlier device applications can therein also be incorporated and used for the parameter evaluation based on the quality criterion, or taken into account for comparison purposes. The quality criterion can also be produced based on a standard procedure, meaning that the parameter will be recorded while a medical procedure knowingly conforming to normal practice is being performed and that the course over time of the parameter registered during the standard procedure will hence be stored as a "good" such course. The quality criteria can therein of course also incorporate mean values extending across different users or medical procedures performed at different times.

The number of user interactions will thus be compared with the mean number of different users' interactions for each application diagnosis or individual application. If the system registers, for example, a significant rise or increase in at least one, preferably two interactions over at least one period of time specified depending on the application, then the system will automatically activate the auxiliary procedure.

The noise level in the area around the system can alternatively or additionally also be registered as a parameter. The noise level, which is to say the volume, or the relative increase in said level during treatment will then be registered for each unit of time. It is therein to be assumed that if complications arise during a medical procedure or if the operator becomes increasingly nervous, the disturbance or, commensurately, the noise level in the system environment, for example the therapy room housing the medical system, will increase and thereby serve as an indicator of the deteriorating conformity of the medical procedure's quality with normal practice.

In particular the number of voice commands uttered by the operator can be registered as a parameter. Voice commands are therein, for example, instructions called to other people by the doctor or a medical assistant acting as the operator of the method.

Multifarious quality criteria are also conceivable in keeping with the wide array of possible parameters. Thus what can be evaluated as quality criteria are, for example, the sequence of therapeutic steps during the procedure, the duration of a therapeutic step, or how often a therapeutic step is repeated. The sequence, duration, and repetition of therapeutic steps are clear indicators of whether a medical procedure is being performed in accordance with normal practice, or with complications or in a manner lacking concentration.

Multifarious embodiments are also conceivable for the above-cited auxiliary procedures.

User prompts specifically tailored to the medical procedure can be displayed to the operator as an auxiliary procedure. That is achieved by, for example, dimming unused keys or touch displays etc. or by selectively illuminating or highlighting keys or touch displays essential for continuing the procedure. The reduction to and focusing on essential functions on the system is achieved thereby and the system made easier for the operator to operate.

On, for example, a monitor belonging to the system it is also possible to display a help icon offering the user a typical workflow based on the selected medical procedure, such as positioning a cardiac catheter. Said function is offered, for example, from the outset independently of the progress of the medical procedure. The icon is, though, varied in its color, for instance (changing, say, to red), immediately upon an essential (system) work step's not having been performed or being performed too slowly or too quickly, or having been repeated too often. The operator will then, by actuating the help button, be able to read through the help information or have it read out aloud over a loudspeaker. Having it read out around therein offers the advantage of imposing no further, visual burden on the operator and additionally having a stress-reducing effect.

It is also possible as an auxiliary procedure for the system's ambient conditions to be adjusted to the operator's needs. Pertinent examples include procedures such as adjusting the light in the room or operating theater by, for instance, amplifying or selectively activating specific additional light sources. The room temperature can also be lowered, for example, or the room humidity reduced.

It is also possible as an auxiliary procedure for the communication scenario around the system to be accommodated to the operator. As an example, communication between the operator and other personnel, for instance with a medical assistant seated outside the radiation area (meaning behind a lead screen) during an X-ray procedure, can be optimized. That is made possible by, inter alia, adjusting the noise level by, for example, selectively activating/deactivating local loudspeakers or selectively orienting microphones.

That is done by, for example, using at least two additional microphones in the operating theater and control room so that the operator will no longer need to shout in order to converse with others but instead be able to speak at normal volume. For example instead of one central microphone in the operating theater, selective communication units can for that purpose be attached directly to medical devices, for example an X-ray device.

It is also possible as an auxiliary procedure to make support personnel available to the operator. In a hospital, for example, a specific ward can be informed automatically. That can be done by means of, for example, a silent alarm for the provisioning of additional personnel when a complication scenario has been registered during the medical procedure.

It is also possible, for instance, if the operator is under stress not to allow any bleeper or call forwarding to said operator until the medical procedure has resumed its normal course or been completed.

By providing a stress-reducing, workflow-oriented system environment as an auxiliary procedure, the operator will therefore be offered essential functions necessary for successfully completing or performing the medical procedure. Expanded, for example inessential or unused functions will be deactivated or their control elements for example dimmed. The area around the system will be stress-optimized for the operator, meaning it will be tailored to the operator's personal requirements. For example the acoustic transmission will for that purpose be adjusted in terms of volume and location and selectively optimized etc.

All auxiliary procedures will ideally be made available throughout the medical procedure in the form of unobtrusive online help.

Thanks to the cited parameters and auxiliary procedures it will therefore in other words be made possible to check the potential weaknesses (for example the room temperature or communication and light conditions) of a special medical system in conjunction with the operator and the medical procedure while that is being performed and, where applicable, to correct them or provide assistance. All the auxiliary procedures will preferably be provided in a clearly organized and unobtrusive manner so that the result for the operator will be assistance or prompting, or guidance in the form of suggested actions.

The object of the invention is achieved in terms of the technical medical system by means of a medical system according to the claims. Thanks to the registering unit the system is therefore suitable for registering the parameter and thanks to the evaluation and control unit it is suitable for evaluating the parameter and initiating the auxiliary measure.

The advantages ensuing from the inventive system have already been explained in connection with the method.

If the registering unit is a counter for the number of operator interactions with the system, then those selfsame interactions can, as described above, be monitored and further processed.

For registering the noise level or voice commands the registering unit can be a microphone.

For monitoring the duration, course etc. of the medical procedure the registering unit can be a detector for the therapeutic step currently being performed which will be identified thereby or whose duration will thereby be allowed to be determined.

The system can have a user-prompting unit for offering the operator the above-cited assistance in terms of the user prompts.

For implementing the above-cited auxiliary procedures in terms of system environment, communication, and operator support from additional personnel, the system can have various interfaces on the evaluation and control unit, particularly to an air-conditioning or lighting-control facility, to a communication unit for the operator, or to a personnel-administration device.

BRIEF DESCRIPTION OF THE DRAWINGS

For a further description of the invention, reference is made to the exemplary embodiments contained in the drawings, both of which are schematic sketches.

FIG. 2 shows the course over time for different interactions made by the doctor with the workstation.

DETAILED DESCRIPTION OF THE INVENTION

Figure 1:
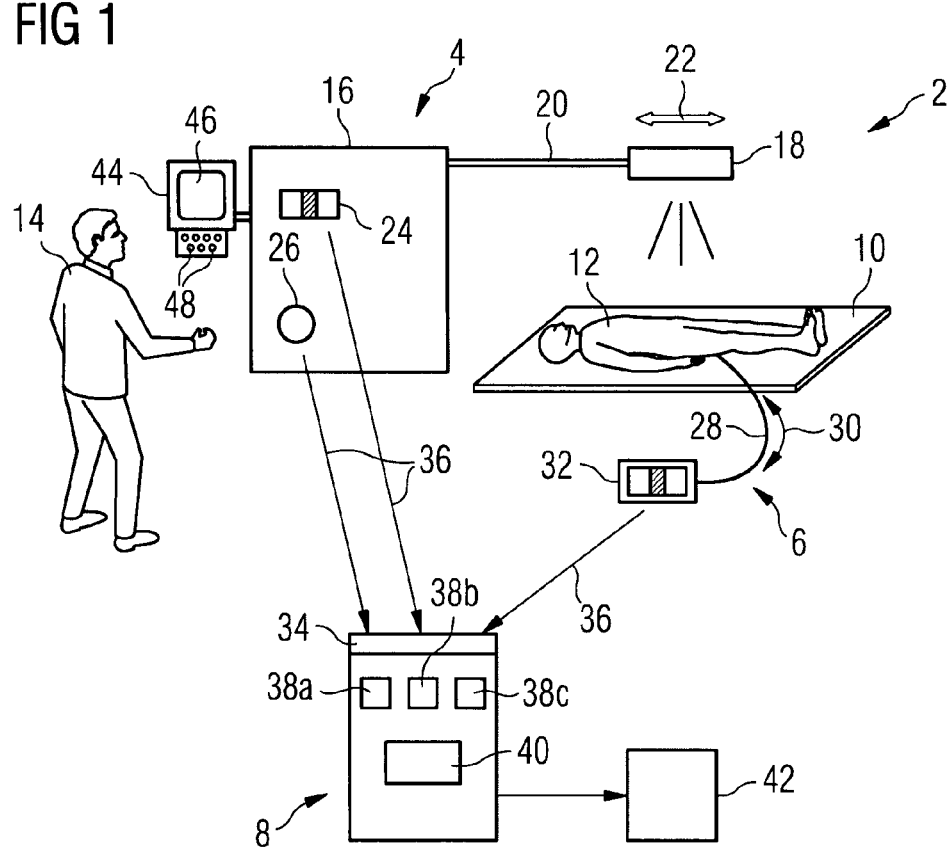
FIG. 1 shows an intervention, for positioning a cardiac catheter, being performed by a doctor on a patient at a medical workstation.

FIG. 1 shows as the medical system 2 a PTCA workstation in a clinic that is not illustrated. A PTCA is to be performed, meaning a balloon catheter is to be ducted into a specific one of a patient's coronary vessels under X-ray irradiation and said vessel widened there. The system 2 includes for that purpose an X-ray device 4, a catheter system 6, and a central computer 8 connected to all other components of the system 2. A patient 12 requiring treatment is positioned on a table 10. A doctor 14 being the operator of the overall system 2 performs the PTCA therapy on the patient 12.

The X-ray device 4 includes a base device 16 to which an X-ray head 18 is secured via a support arm 20. The X-ray head 18 can be moved in the direction of the double arrow 22 relative to the patient 12 on the table 10 so that the patient 12 can be X-rayed from different viewing angles and different views thus obtained of the catheter and coronary vessels. The X-ray head 18 is moved by means of a slider control 24, operated by the doctor 14, on the base device 16. The doctor 14 produces an X-ray image 46 of the patient 12 on a monitor 44 by operating a trigger button 26 on the base device 16.

The catheter system 6 has a catheter 28, inserted into the patient 12, that can be moved inside the patient 12 in the direction of the double arrow 30. It is therein moved under the control of the doctor 14 in such a way as to actuate a slider control 32 on the catheter system 6.

The computer 8 includes a detector 34 which (indicated by the arrows 36) monitors the slider controls 24 and 32 and the trigger button 26 for their being operated. Said monitoring takes place continuously throughout the intervention performed on the patient 12. From monitoring of the three just-cited control elements the detector 34 produces three parameters 38$a$-$c$ each indicating how often the relevant element has been actuated per unit of time.

FIG. 2 shows the course over time of the parameters 38$a$-$c$ from the start of the treatment performed on the patient 12 at the instant $t_1$ until the end thereof at the instant $t_2$. The value of the parameters 38$a$-$c$ has thus in the diagram in FIG. 2 been entered on the ordinate opposite the time t on the abscissa in the form of the number $N_a$, $N_b$, $N_c$ of interactions. The parameter 38$a$ therein represents the number $N_a$ of X-ray operations initiated by the trigger button 26 and is indicated in FIG. 2 by means of dashed lines. The parameter 38$b$ describes the number of actuations of the slider control 24 and hence how often the X-ray head 18 has been moved, and is represented in FIG. 2 by means of a broken line. The parameter 38$c$ indicates how often the slider control 32 has been operated and hence how often the catheter 28 has been moved inside the patient, and is represented in FIG. 2 by means of a solid line.

The intervention performed on the patient 12 proceeds normally from the instant $t_1$ until the instant $t_3$, meaning that the doctor 14 advances the catheter 28 toward the coronary vessels of the patient 12 with a small number of X-ray images, changes in the position of the X-ray head 18, and corrections in the catheter's advancement. The doctor determines at the instant $t_3$ that he/she has not yet located the required coronary vessel in the patient 12. The doctor 14 becomes nervous and increases the number of X-ray operations (parameter 38$a$), repositions the X-ray head 18 frequently, and moves the catheter 28 back and forth frequently. There is hence a significant rise in the parameters 38$a$-$c$ indicating how often the relevant control elements have been actuated on the system 2.

Stored in the computer 8 is a quality criterion 40 against which the parameters 38$a$-$c$ are continuously evaluated. The quality criterion 40 corresponds in the present example to the fact that the number of relevant control procedures performed by the doctor 14 on the system 2 must not exceed a limiting value, meaning a specific number $N_g$. An auxiliary procedure 42 will according to the quality criterion be initiated by the computer 8 when at least two of the parameters 38$a$-$c$ have exceeded the limiting value $N_g$.

The parameter 38$a$ exceeds the limiting value $N_g$ at the instant $t_4$, meaning that the doctor 14 has been operating the X-ray head 18 via the trigger button 26 unusually frequently. At the instant $t_5$ the parameter 38$c$ also exceeds the limiting value $N_g$, meaning that the doctor 14 has been moving the catheter an above-average number of times by actuating the slider control 32. An auxiliary procedure is therefore initiated at the instant $t_5$ as a procedure 42 through which two operating controls 48 for adjusting the brightness and contrast of the X-ray image 46 are back-illuminated more intensely for the doctor 14 on the monitor 44 and the remaining operating controls 48 dimmed. That is because the nervousness of the doctor 14 starting at the instant $t_3$ is due to his/her not locating the required coronary vessel in the X-ray image 46 owing, namely, to the incorrect brightness and contrast setting for the image. Thus through the auxiliary procedure 42, which is to say through highlighting of the relevant operating controls 48, the doctor will be prompted or reminded to display the X-ray image 46 better. He/she will thereupon detect the required coronary vessel and move the catheter 28 accordingly, and will by the instant $t_6$ have positioned the catheter 28 correctly. Because the parameters 38$a$-$c$ are again falling below the limiting value $N_g$ at the instant $t_6$, the quality criterion 40 will have been met and the auxiliary procedure 42 can be discontinued. The relevant system procedures for relieving the stress experienced by the doctor 14 have therefore been successful and he/she continues providing the treatment in a stress-free manner and in accordance with normal practice until its completion at the instant $t_2$.

The invention claimed is:
1. A computerized method for operating a medical system by an operator during a procedure, comprising:
continuously registering a parameter correlated with a quality of a performance of the procedure while per- forming the procedure wherein the parameter comprises counting the number of times a step in the procedure is repeated;

evaluating the parameter based on a predetermined quality criterion correlated with a fault-free performance of the procedure step wherein the procedure is performed fault free when the total number of times the procedure step is performed does not exceed a predetermined maximum number of times that the procedure step is performed;

detecting motion made by the operator for actuating a control of the medical system wherein actuation of the control directs operation of a device used in the procedure and generates the parameter;

initiating an auxiliary procedure when the parameter violates the predetermined quality criterion for performing the procedure step correctly; and providing a computer for performing the steps of continuously registering a parameter, evaluating the parameter and initiating an auxiliary procedure wherein the parameter is stored in the computer.

2. The method as claimed in claim 1, wherein the parameter comprises a number of interactions between the operator and the medical system.

3. The method as claimed in claim 1, wherein the predetermined quality criterion is a maximum number of the interactions.

4. The method as claimed in claim 1, wherein the parameter comprises a noise level in an area around the medical system.

5. The method as claimed in claim 4, wherein the noise level comprises a number of voice commands uttered by the operator.

6. The method as claimed in claim 1, wherein the predetermined quality criterion is selected from the group consisting of: a sequence of therapeutic steps during the procedure, and a duration of a therapeutic step, and how often a therapeutic step is repeated.

7. The method as claimed in claim 1, wherein the auxiliary procedure comprises displaying a user prompt specifically tailored to the procedure to the operator.

8. The method as claimed in claim 1, wherein the auxiliary procedure comprises adjusting an ambient condition of the medical system to a need of the operator.

9. The method as claimed in claim 1, wherein the auxiliary procedure comprises accommodating a communication scenario around the medical system to the operator.

10. The method as claimed in claim 1, wherein the auxiliary procedure comprises making a support personnel available to the operator.

11. A computerized medical system operated by an operator for performing a procedure currently being performed, comprising:

a registering unit that continuously registers a parameter correlated with a quality of a performance of the procedure while performing the procedure wherein the parameter comprises counting the number of times a step in the procedure is repeated; and an evaluation and control unit that:

evaluates the parameter based on a predetermined quality criterion correlated with a fault-free performance of the procedure step wherein the procedure is performed fault-free when the total number of times the procedure step is performed does not exceed a predetermined maximum number of times that the procedure step is performed;

initiates an auxiliary procedure when the parameter violates the predetermined quality criterion for performing the procedure step correctly;

a detector for detecting motion made by the operator for actuating a control of the medical system wherein actuation of the control directs operation of a device used in the procedure and generates the parameter; and a computer for operating the registering unit and the evaluation and control unit wherein the parameter is stored in the computer.

12. The medical system as claimed in claim 11, wherein the registering unit is a counter and the parameter is a number of operator interactions with the system.

13. The medical system as claimed in claim 12, wherein the predetermined quality criterion is a maximum number of the interactions.

14. The medical system as claimed in claim 11, wherein the registering unit is a microphone and the parameter is a noise level in an area around the medical system.

15. The medical system as claimed in claim 11, wherein the registering unit is a detector that identifies a currently performed therapeutic step.

16. The medical system as claimed in claim 15, wherein the predetermined quality criterion is selected from the group consisting of: a sequence of therapeutic steps during the procedure, and a duration of a therapeutic step, and how often a therapeutic step is repeated.

17. The medical system as claimed in claim 11, further comprising a user-prompting unit and the auxiliary procedure comprises displaying a user prompt specifically tailored to the procedure to the operator.

18. The medical system as claimed in claim 11, wherein the evaluation and control unit comprises an interface to an air-conditioning or lighting-control facility and the auxiliary procedure comprises adjusting an ambient condition of the medical system to a need of the operator.

19. The medical system as claimed in claim 11, wherein the evaluation and control unit comprises an interface to a communication unit for the operator and the auxiliary procedure comprises accommodating a communication scenario around the medical system to the operator.

20. The medical system as claimed in claim 11, wherein the evaluation and control unit comprises an interface to a personnel-administration device and the auxiliary procedure comprises making a support personnel available to the operator.

* * * * *